(12) United States Patent
Nguyen et al.

(10) Patent No.: US 11,334,570 B2
(45) Date of Patent: May 17, 2022

(54) BLOCKCHAIN-SECURED AND DOCUMENT-BASED ELECTRONIC MEDICAL RECORDS SYSTEM

(71) Applicant: Francis Tuan Anh Nguyen

(72) Inventors: Francis Tuan Anh Nguyen, Ho Chi Minh (VN); Duy Vu Minh Nguyen, Ho Chi Minh (VN)

(73) Assignee: INFOMED VIET NAM, Ha Noi (VN)

(*) Notice: Subject to any disclaimer, the term of this patent is extended or adjusted under 35 U.S.C. 154(b) by 268 days.

(21) Appl. No.: 16/676,422

(22) Filed: Nov. 6, 2019

(65) Prior Publication Data

US 2021/0133197 A1 May 6, 2021

(51) Int. Cl.
*G06F 16/2457* (2019.01)
*G06F 16/21* (2019.01)
*G06F 16/23* (2019.01)
*H04L 9/32* (2006.01)
*G16H 10/60* (2018.01)
*H04L 9/06* (2006.01)

(52) U.S. Cl.
CPC ...... *G06F 16/24573* (2019.01); *G06F 16/211* (2019.01); *G06F 16/2379* (2019.01); *G16H 10/60* (2018.01); *H04L 9/0643* (2013.01); *H04L 9/3247* (2013.01); *H04L 2209/38* (2013.01)

(58) Field of Classification Search
None
See application file for complete search history.

(56) References Cited

U.S. PATENT DOCUMENTS

| | | | | |
|---|---|---|---|---|
| 6,968,503 B1* | 11/2005 | Chang | | G06Q 10/10 715/202 |
| 7,716,072 B1* | 5/2010 | Green, Jr. | | G06Q 10/10 705/3 |
| 8,352,444 B1* | 1/2013 | Chang | | G06F 16/93 707/694 |

(Continued)

OTHER PUBLICATIONS

Liviu Hirtan et al, "Blockchain-based approach for e-health data access management with privacy protection", IEEE 2019, 7 pages.*

(Continued)

*Primary Examiner* — Uyen T Le
(74) *Attorney, Agent, or Firm* — Keith Kline; The Kline Law Firm PC

(57) ABSTRACT

An electronic medical records (EMR) system that enables a user to import paper-based clinical form templates (typically Word documents) and insert data tags in the data fields on the templates. This approach allows the user to retrieve clinical data from user inputs and from hospital recordkeeping systems, such as HIS, LIS, RIS/PACS, and others to generate EMR forms. Medical personnel can then access the data to generate descriptive, predictive, or prescriptive analytics including vital sign charts, drug interaction warnings, and drug recommendations. The system also enables secure data sharing between healthcare facilities using a blockchain system or a FHIR server. Upon signing an EMR form with one or more electronic signatures, the system generates a digitized image including images of the electronic signatures. The system generates hash of the digitized image and store the hash to the blockchain system, wherein the hash is used to verify the signed EMR form.

20 Claims, 5 Drawing Sheets

(56) References Cited

U.S. PATENT DOCUMENTS

| | | | | |
|---|---|---|---|---|
| 2007/0288268 A1* | 12/2007 | Weeks | ............... | G16H 10/60 |
| | | | | 705/3 |
| 2011/0119089 A1* | 5/2011 | Carlisle | ............. | G16H 10/60 |
| | | | | 705/3 |
| 2011/0276349 A1* | 11/2011 | Huang | ............... | G16H 10/20 |
| | | | | 705/3 |
| 2018/0218779 A1* | 8/2018 | Collins, Jr. | ......... | H04L 9/3297 |
| 2019/0213333 A1* | 7/2019 | Williams | ............ | H04L 9/3242 |
| 2019/0304582 A1* | 10/2019 | Blumenthal | ........ | G06F 9/451 |
| 2021/0169576 A1* | 6/2021 | Yoshinaka | .......... | G16H 10/60 |

OTHER PUBLICATIONS

Lotfi Tamazirt et al, "Blockchain Technology: A new secured Electronic Health Record System", Proceedings ASVANCE 2018, 9 pages.*

Andrianov et al, "Blockchain in Clinical Trials—the Ultimate Data Notary", Applied Clinical Trials, Jul./Aug. 2018, 5 pages.*

* cited by examiner

BLOCKCHAIN-SECURED AND DOCUMENT-BASED ELECTRONIC MEDICAL RECORDS SYSTEM

BACKGROUND

Field of the Invention

The present disclosure relates to the digital transformation of healthcare systems, and more particularly, to systems and methods for providing electronic medical records.

Description of the Related Art

A patient's medical records are often contained in multiple paper-based clinical forms (e.g., physicians' diagnoses, laboratory test results, medicine prescriptions) and films (e.g., x-rays images, magnetic resonance imaging (MRI) scans). Healthcare professionals (HCP) must have access to all these paper forms and films to provide the optimal treatment for their patients.

Most existing hospital information systems (HIS) attempt to consolidate the patient's medical records by adding/modifying HIS screens to capture additional patient data to produce a Portable Document Format (PDF)-based EMR. However, this approach has several drawbacks. First, using HIS screens is not as natural as using document-based clinical forms to capture patient data as patients are examined. Second, when content and/or layout changes, coding is required to add or modify HIS screens. Third, data mining cannot be applied to the data in the PDF-based EMR for descriptive, predictive, and prescriptive analytics such as visualizing vital signs, predicting drug interaction, recommending alternative drugs to replace given drugs that interact, etc.

SUMMARY

The present invention is an electronic medical records (EMR) system that supports importing paper-based clinical form templates like importing Word documents. After the forms are imported, the present invention supports replacing the data fields in the forms with data tags that can retrieve data from user inputs, from hospital systems of record such as a hospital information system (HIS), a laboratory information system (LIS), a radiological information system/picture archiving and communication system (RIS/PACS), and from medical equipment. Using the current invention, healthcare professionals can capture patient data as the patients are examined.

The present invention makes modifying a paper-based form as easy as editing a Word document, and thus requires no code changes when content and/or layout changes.

The present invention stores all data tags as in-memory JavaScript Object Notation (JSON) tuples so patient data can be quickly data mined for descriptive, predictive, and prescriptive analytics like visualizing vital signs, predicting drug interactions, recommending alternative drugs to replace interacting drugs, etc.

The present invention allows the EMR to be signed using electronic signature certified by a blockchain system and to be shared within and between hospitals as easily as any other electronic documents, or to be shared using a Fast Healthcare Interoperability Resources (FHIR) server.

According to one example embodiment, a computer-implemented method for providing EMRs is disclosed. The method may include receiving a generic word-processing form template. The method may include enabling completing data fields in the generic word-processing form template with data tags and action tags to generate an EMR form. The data tags and action tags can be used to enable retrieval and storage of clinical data associated with a patient. The clinical data can be supplied via user input or hospital records systems. The method may include enabling signing the EMR form with one or more electronic signatures. The method may also include, upon signing the EMR form, generating a digitized image including images of the one or more electronic signatures. The method may then proceed with generating a hash based on the digitized image. The method may also include storing the signed EMR form in an EMR data repository. The method may then proceed with storing the hash to a blockchain system. The hash can be used to verify the signed EMR form.

According to another embodiment, a system for providing EMRs is disclosed. The system may include at least one processor and a memory storing processor-executable codes, wherein at least one processor can be configured to implement operations of the above-mentioned method for providing EMRs upon execution of the processor-executable codes.

According to yet another aspect of the disclosure, there is provided a non-transitory processor-readable medium, which stores processor-readable instructions. When the processor-readable instructions are executed by a processor, they can cause the processor to implement the above-mentioned method for providing EMRs.

Additional objects, advantages, and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities, and combinations particularly pointed out in the appended claims.

DETAILED DESCRIPTION

Figure 1:
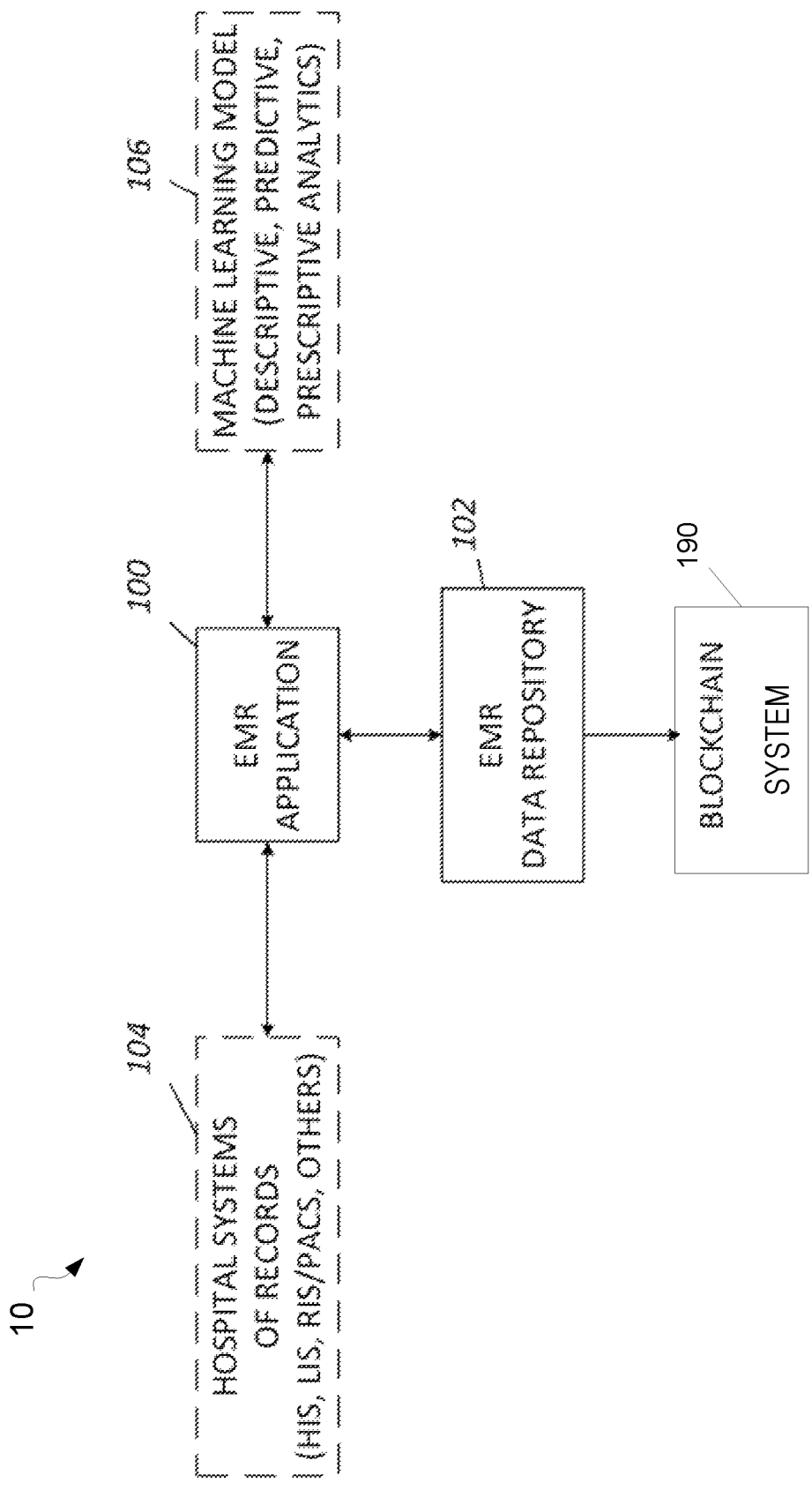
FIG. 1 is a block diagram illustrating the electronic medical records (EMR) system

The present disclosure relates to systems and methods for providing EMRs. Embodiments of present disclosure facilitate transforming non-electronic medical records (paper and film) to the EMRs. The EMRs can be stored on portable computing devices (laptops, tablets, and phones) used by the healthcare professionals during examination and backed up to hospital server at the end of the day, at the end of an examination, or at other predetermined intervals. Embodiments of the present disclosure may allow signing the EMRs using electronic signatures certified by a blockchain system. The EMRs can be shared within and between hospitals as easily as any other electronic documents. The sharing of the EMRs can be facilitated (and authenticated) by the blockchain system or a FHIR server.

According to an example embodiment, A system for providing electronic medical records (EMRs) is disclosed. The system can include at least one processor and a memory storing one or more applications as processor-executable codes, wherein upon executing the processor-executable codes, at least one processor can receive a generic word-processing form template. The processor can facilitate completing data fields in the generic word-processing form template with data tags and action tags to generate an EMR form. The data tags and the action tags can be used to enable retrieval and storage of clinical data associated with a patient. The clinical data can be supplied via a user input or hospital records systems. The processor may enable signing the EMR form with an electronic signature. Upon signing the EMR form, the processor can generate a digitized image including images of the one or more electronic signatures. The processor may then generate a hash based on the digitized image. The processor may store the signed EMR form to an EMR data repository and store the hash to a blockchain system. The hash can be used to verify the signed EMR form.

The clinical data can be collected when the patient is examined. The hospital records systems may include hospital information systems, laboratory information systems, radiological information systems, and picture archiving and communication systems.

The system may further include an EMR data repository configured to store generic word-processing form templates, clinical data, and EMR forms. The EMR forms can be shared on a limited time basis with other parties.

The processor can perform, via machine learning model, descriptive analytics, predictive analytics, and prescriptive analytics on the clinical data. The descriptive analytics can be performed using Power BI. The predictive analytics and the prescriptive analytics can be performed using Azure Machine Learning or Microsoft Cognitive Toolkit. The descriptive analytics can also be performed using Tableau. The predictive analytics and the prescriptive analytics can be performed using TensorFlow. The processor may update the machine learning model upon establishing connection to the Internet.

The applications can be configured to run on Windows based laptops, Android based tablets, and/or on iPads with Apple Pencil. The applications can be configured to run as desktop applications, web applications, word applications, or mobile applications. The user input can be received via a keyboard, mouse, handwriting device, voice input device, or other input device.

The clinical data can be retrieved from hospital records systems via at least one of application programming interface or a stored procedure.

The system may include a backup mechanism configured to back up system data at predefined time intervals. The system data include one or more generic word-processing form templates, one or more EMR forms, and clinical data.

The processor may enable sharing, via the blockchain system or a Fast Healthcare Interoperability Resources (FHIR) server, the system data to healthcare facilities. The data tags and action tags can be updated upon establishing connection to the Internet. The EMR data repository can include a NoSQL database. The processor may back up the NoSQL database to Microsoft Azure, Amazon Web Services, or Google Cloud Platform upon establishing connection to the Internet.

FIG. 1 illustrates the architecture of the EMR system 10. Healthcare professionals capture and access patient data using an EMR application 100 that stores and retrieves such data from an EMR Data Repository 102. The EMR application 100 also communicates with the Hospital Systems of Records 104 to obtain patient data, such as laboratory test results and X-ray images. The EMR data repository 102 transfers patient information from the EMR system to other healthcare providers after certifying the electronic signatures of the EMR forms via a blockchain system and sharing the EMR forms as electronic documents or using a FHIR server. The EMR application 100 captures patient data in real-time at the point of care, where healthcare providers interact with their patients. As the EMR application 100 captures patient data, it may ask the machine learning model 106 to analyze this data for descriptive purpose (e.g., visualizing vital signs), predictive purpose (e.g., predicting drug interaction), or prescriptive purpose (e.g., recommending alternative drugs to replace the given drugs which interact).

Figure 2:
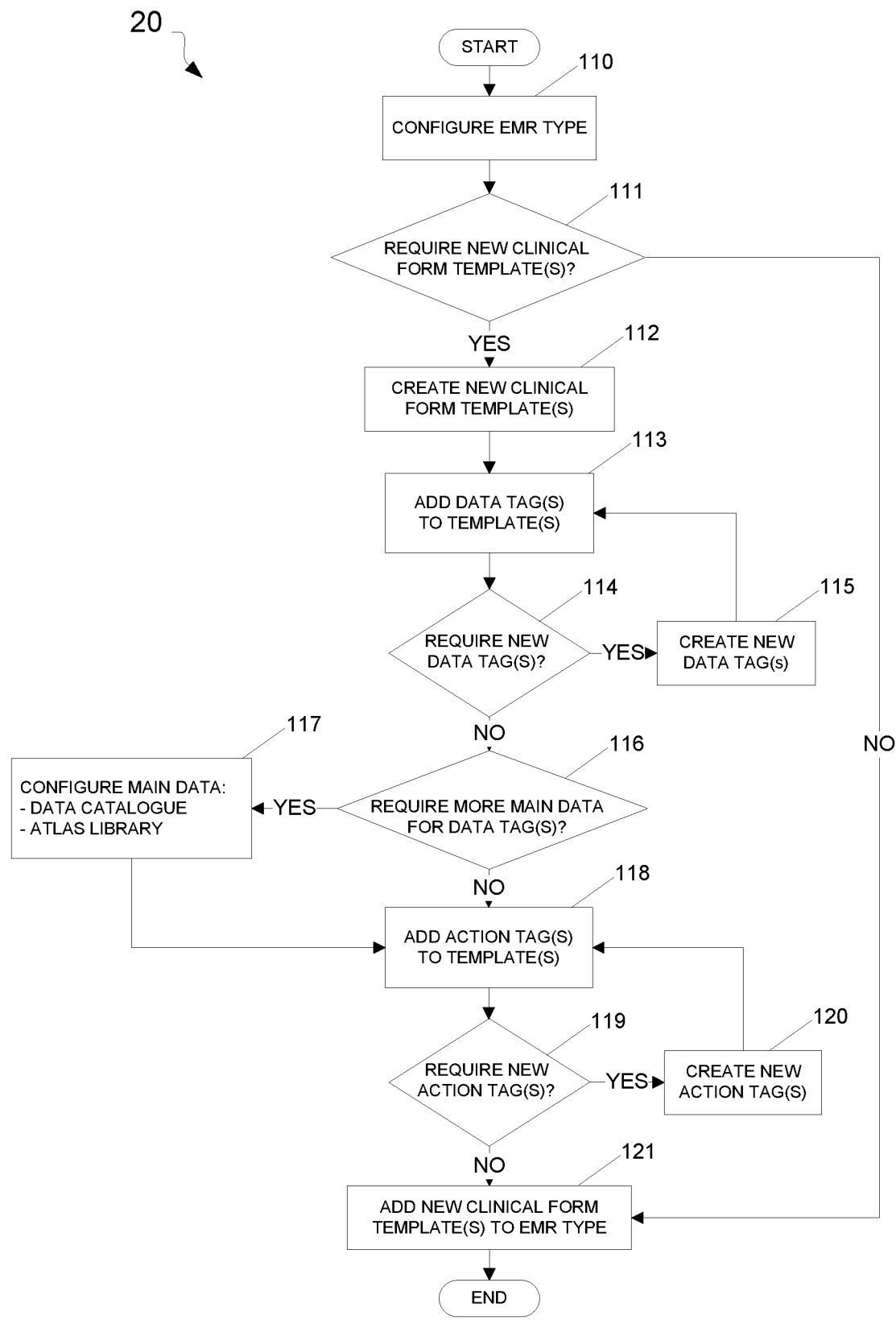
FIG. 2 is a flowchart illustrating the process flow followed by those who will design the clinical form template(s) of the EMR system of the present invention.

The flow chart in FIG. 2 illustrates the process 20 followed by designers of the clinical form template(s) of the EMR system 10. A designer can be either a system integrator or hospital IT personnel. The forms can be designed by a system integrator and handed over to hospital IT personnel for maintenance or designed by hospital IT personnel at the start.

The process 20 begins with a designer specifying the EMR type in step 110, e.g., outpatient.

Once the EMR type has been established, the designer checks in step 111 to determine whether the EMR type requires one or more new clinical form template(s). If a new template is required, the designer creates one or more new clinical form template(s) in step 112.

After the new template(s) are created, the designer adds data tags to the new template(s) in step 113. If in step 114, the designer determines that new data tags are required, the designer creates the new data tags in step 115. The designer is then able to and repeat the cycle of steps 113-114-115 as required. While creating the data tags, the designer checks if main data is required in step 116 and configures the required main data in step 117. The main data may include master data such as list of drugs or list of laboratory tests exported from other hospital systems of records (e.g., HIS) and imported into the EMR application.

In step 118, the designer adds the action tags to the template(s). If it is determined that further new action tags are required in step 119, the designer then creates the action tags in step 120 and repeats the cycle of steps 118-119-120 as required. The action tags may include macros which can retrieve a series of data tags.

Finally, the designer adds existing/new clinical form template(s) to the EMR type in 121.

Figure 3:
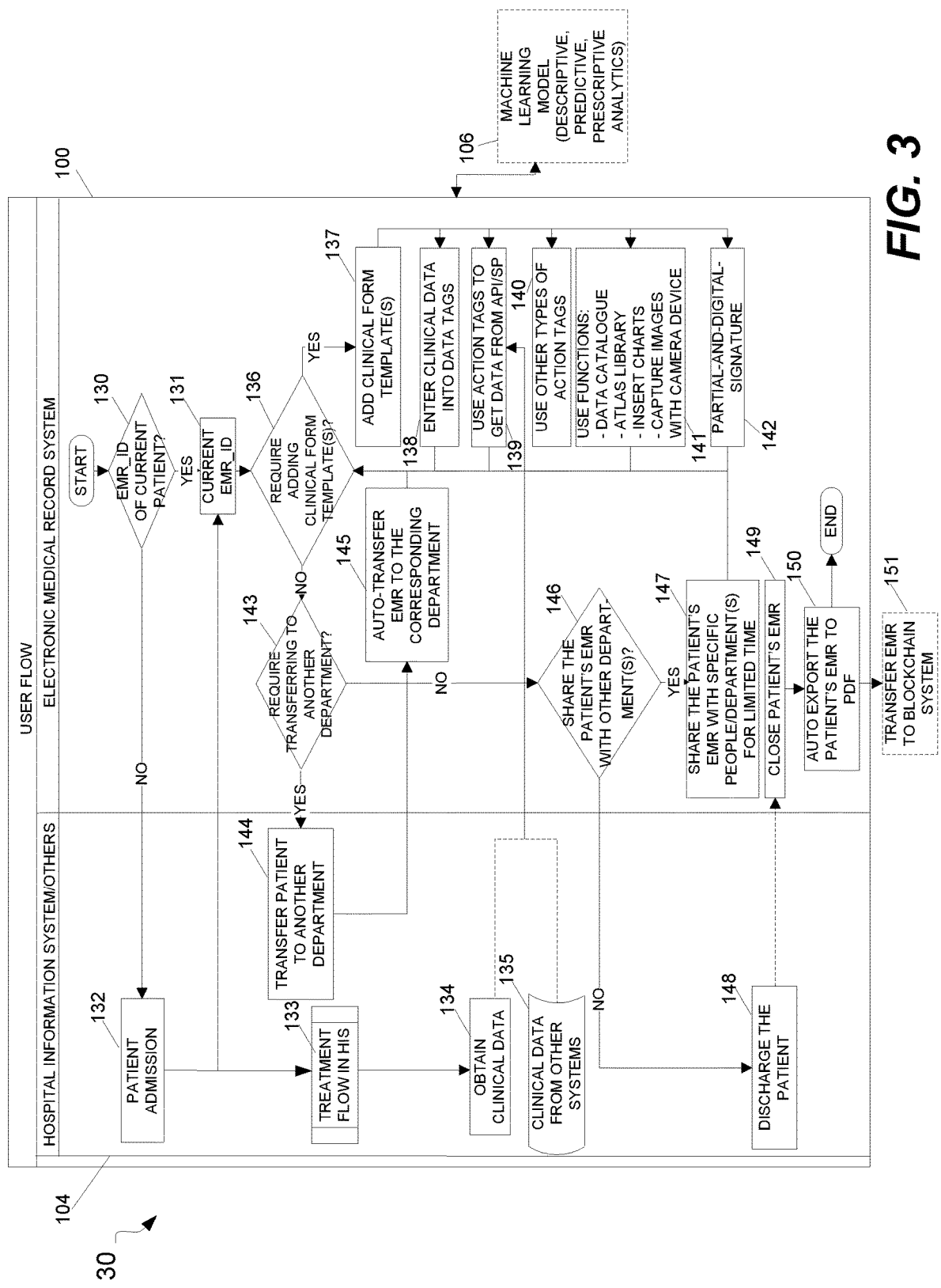
FIG. 3 is a flowchart illustrating the process flow followed by those who will use the clinical form template(s) of the EMR system of the present invention.

Upon completion of the template generation process described above, the required clinical form templates of the EMR system are available for users as illustrated in FIG. 3. A user may be any healthcare professional (HCP) or the like.

Referring now to FIG. 3, a process 30 of use of the EMR system 10 is shown. The use of the EMR system may be accomplished as follows: The HCP must check to confirm in step 130 that the subject EMR_ID is that of the current patient. If confirmed, the current EMR_ID is established as indicated in step 131. However, if the ID cannot be confirmed, the HCP transfers the EMR_ID to the HIS 104 for patient admission in step 132.

If the ID is confirmed for the patient as the current EMR_ID, the HCP checks to see if the EMR requires adding any clinical form templates in step 136. If yes, the HCP adds clinical form template(s) in step 137.

During the examination of the patient, the HCP enters clinical data into data tags in step 138. The HCP may use action tags to get clinical data from an Application Programming Interface (API) or a Stored Procedure (SP) in step 139. The APIs and SPs can be defined and agreed upon between the EMR application and other hospital systems of records such that the EMR application can retrieve data from these systems. The APIs and SPs can be implemented by the providers of the hospital systems of records. The HCP may also use other types of action tags in step 140, and apply certain functions in step 141. Some of the functions that can be applied include conversion functions like number-to-string, upper-to-lower case, and so forth. The HCP then digitally signs the EMR, or at least some sections of the EMR, in step 142. The HCP repeats the cycle of steps 136-142 as required.

Using action tags in step 139, the HCP transfers the clinical data from the HIS and other Hospital Systems of Records 104 (LIS, RIS/PACS, etc.) to the EMR in 134 and 135. The clinical data from the other systems in 135 can be obtained via the same way as in 134, i.e., via the APIs or SPs provided by the other systems.

During the examination, the HCP can ask the Machine Learning Model (MLM) 106 for descriptive, predictive, or prescriptive analytics of the clinical data. An example of descriptive analytics is the HCP asking the MLM to present different visuals (e.g., line chart) or highlight abnormal values (e.g., red-highlight high values) on selected data (e.g., vital signs). An example of predictive analytics is the HCP asking the MLM to predict interaction among the given drugs in a prescription. An example of prescriptive analytics is the HCP asking the MLM to recommend alternative drugs to replace the given drugs which interact.

After the examination is complete, the HCP checks to see if the patient needs to be transferred to another department in step 143 by checking whether additional medical examinations or tests needed to be performed by another department. If the patient does need to be transferred, the HCP transfers the EMR_ID to the HIS for patient transfer in step 144. The EMR will be automatically transferred to the appropriate department in step 145. At this point, the HCP may repeat the cycle of steps 136-142 until all the required clinical form templates are added to the EMR for the department the patient has been transferred to.

The HCP checks to determine if the EMR needs to be shared with other departments in step 146. If yes, the EMR will be shared with the other departments in step 147. The sharing of the EMR may be on a time limited basis.

When treatment is complete, the HCP discharges the patient using the HIS in step 148. When the patient is discharged, the EMR is closed in step 149 and auto-exported to PDF format in step 150.

The EMR forms or sections within a form can be signed electronically with one or more electronic signatures. The electronic signatures may include digital codes or generated images of handwritten signatures. The signed content as well as the electronic signature can then be stored as a block in a blockchain system. The signed EMR forms can be converted to a digitized image, wherein the digitized image includes images of the electronic signatures. A hash function can be applied to the digitized image to generate a hash. The hash can be stored to the blockchain system as an immutable block. This electronic signing certified by a blockchain system is cheaper and simpler than requiring a verified digital signature and establishes with absolute certainty the indisputability and responsibility of the signer for the signed content. Once electronically signed and certified via a blockchain system, the EMR forms can be shared within and between hospitals as electronic documents. In addition, the EMR forms can be shared using a FHIR server.

Upon receiving a request for a verification/authentication of a signed EMR form, HIS or FHIR server can generate a digitized image including images of signatures in the EMR form. The HIS or FHIR server can generate, based on the digitized image, a hash and then the generated hash can be compared to the hash of the EMR form stored in blockchain system. The blockchain system stores hashes of EMR forms in immutable blocks. Therefore, once being generated, the hash of the signed EMR form remains the same on the blockchain. This allows verification/authentication of the signed EMR using different FHIR servers and HISs of different hospitals. It should be also noted that a single EMR form can include multiple signatures and/or initials. Therefore, by generating a hash for the EMR form including multiple signatures and storing the hash to an immutable block of blockchain, all signatures in the EMR form can be effectively verified using the same hash and by performing a single request to the blockchain system for verification. This allows eliminating verifications of each of the signatures in the EMR form separately, and therefore, reduces the time needed for verifications.

Figure 4:
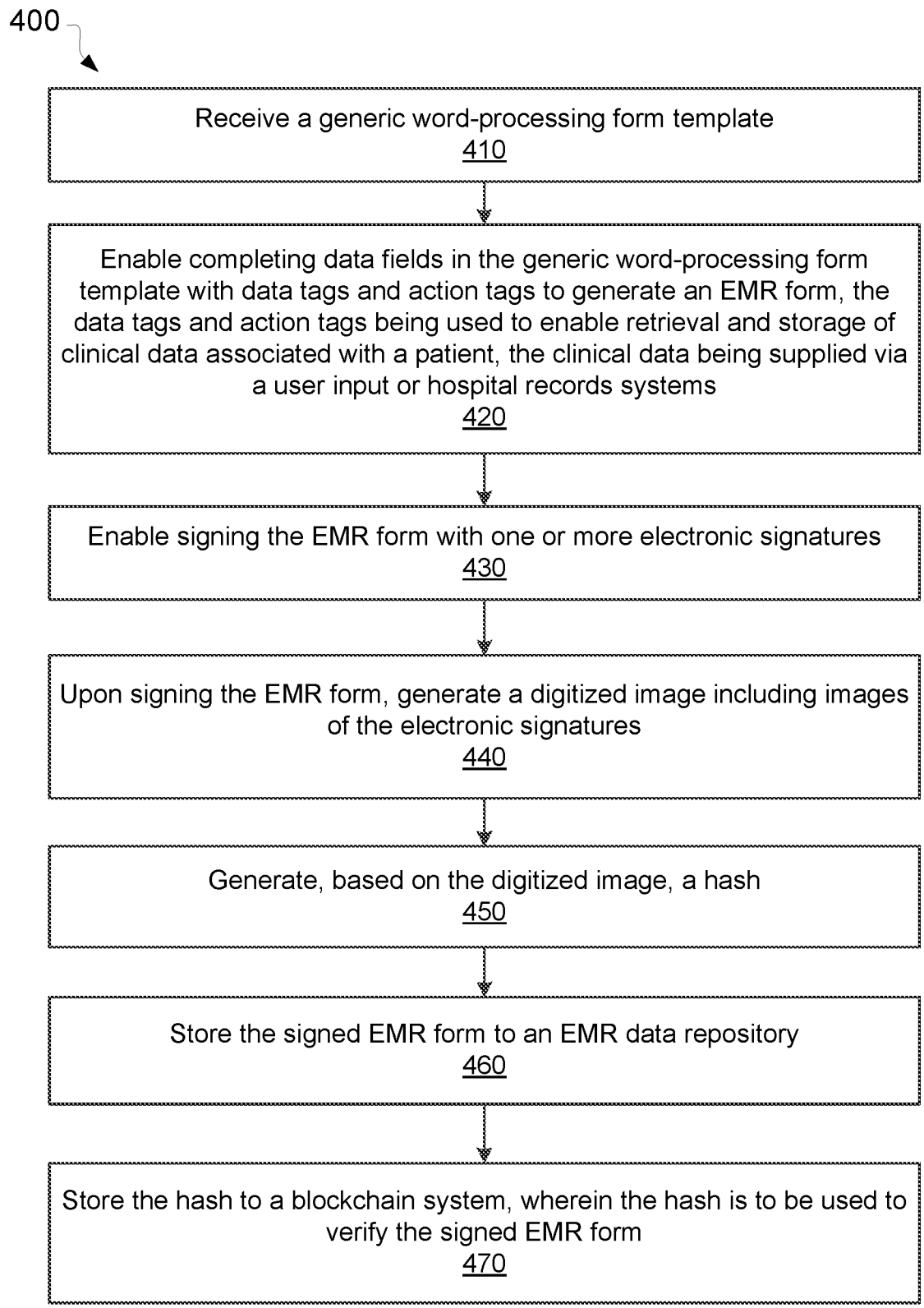
FIG. 4 is a flow chart showing steps of method for providing EMRs, according to an example embodiment.

FIG. 4 is a flow chart showing steps of method 400 for providing EMRs, according to an example embodiment. The method 400 can be implemented by EMR system 10 shown in FIG. 1. The method 400 may commence in block 410 with receiving a generic word-processing form template.

In block 420, the method 400 may proceed to enable completing data fields in the generic word-processing form template with data tags and action tags to generate an EMR form. The data tags and action tags can be used to enable retrieval and storage of clinical data associated with a patient. The clinical data can be supplied via a user input or hospital records systems.

In block 430, the method 400 can proceed with enabling signing the EMR form with one or more electronic signatures.

In block 440, the method 400 may proceed, upon signing the EMR form, with generating a digitized image including images of the electronic signatures.

In block 450, the method 400 may proceed with generating a hash based on the digitized image.

In block 460, the method 400 may store the signed EMR form to an EMR data repository.

In block 470, the method 400 may store the hash to a blockchain system such that the hash can be subsequently used to verify the signed EMR form.

Figure 5:
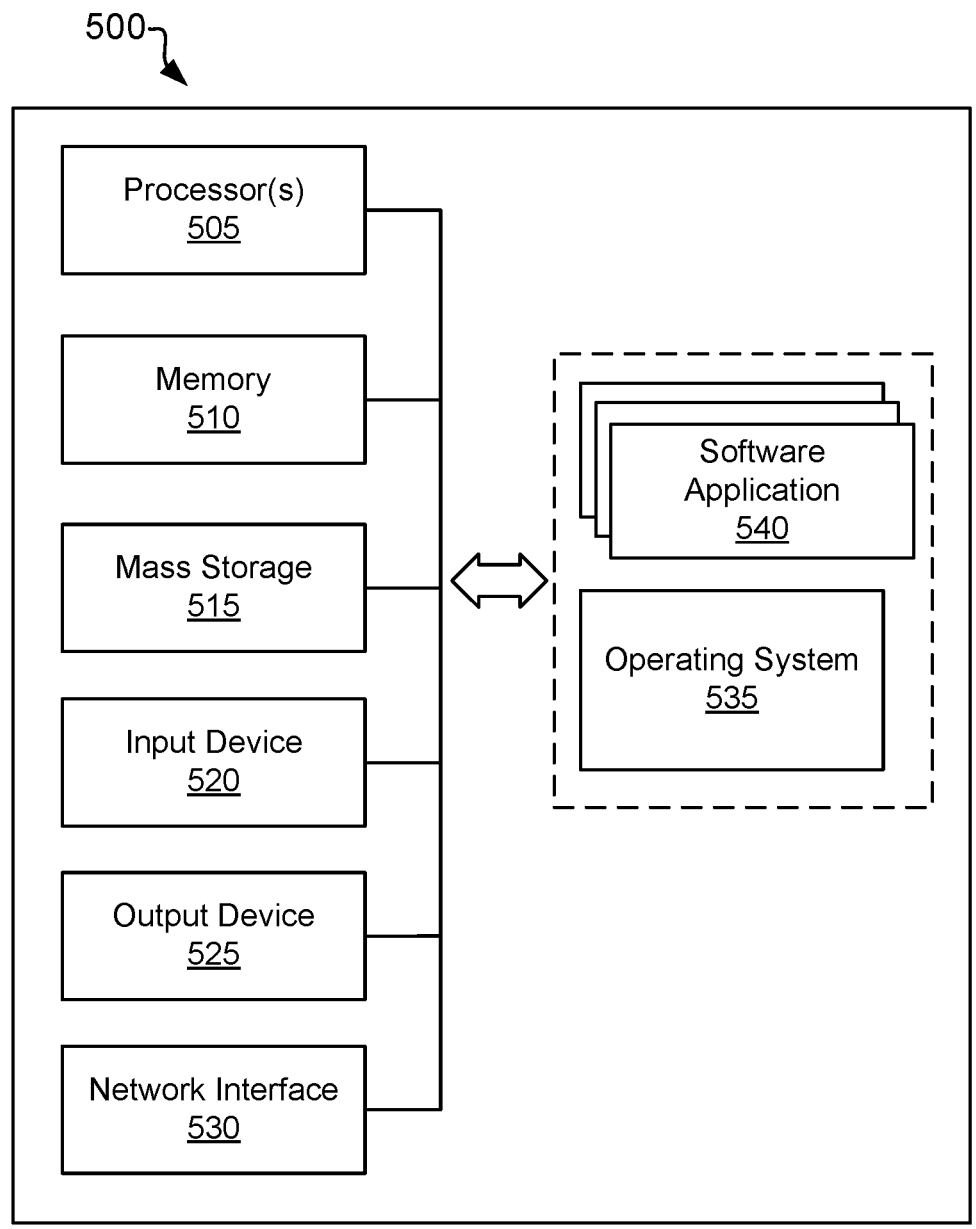
FIG. 5 is a high-level block diagram illustrating an example computer system, within which a set of instructions for causing a machine to perform any one or more of the methodologies discussed herein can be executed.

FIG. 5 is a high-level block diagram illustrating an example computer system 500, within which a set of instructions for causing the machine to perform any one or more of the methodologies discussed herein can be executed. The computer system 500 can refer to or be an integral part of one or more of a variety of types of devices, such as a general-purpose computer, desktop computer, laptop computer, tablet computer, netbook, mobile phone, smartphone, personal digital computer, smart television device, server, among others. In some embodiments, the computer system 500 can be implemented in the contexts of the likes of EMR application 100, system 104, machine learning model 106, and blockchain system 190. Notably, FIG. 5 illustrates just one example of the computer system 500 and, in some embodiments, the computer system 500 may have fewer elements/modules than shown on FIG. 5 or more elements/modules than shown on FIG. 5.

The computer system 500 includes one or more processors 505, a memory 510, one or more storage devices 515, one or more input devices 520, one or more output devices 525, and network interface 530. One or more processors 505 are, in some examples, configured to implement functionality and/or process instructions for execution within the computer system 500. For example, the processors 505 may process instructions stored in memory 510 and/or instructions stored on storage devices 515. Such instructions may include components of an operating system 535 or software applications 540. Computer system 500 may also include one or more additional components not shown in FIG. 5, such as a housing, power supply, battery, global positioning system (GPS) receiver, and so forth.

Memory 510, according to one example, is configured to store information within the computer system 500 during operation. Memory 510, in some example embodiments, may refer to a non-transitory computer-readable storage medium or a computer-readable storage device. In some examples, memory 510 is a temporary memory, meaning that a primary purpose of memory 510 may not be long-term storage. Memory 510 may also refer to a volatile memory, meaning that memory 510 does not maintain stored contents when memory 510 is not receiving power. Examples of volatile memories include random access memories (RAM), dynamic random access memories (DRAM), static random access memories (SRAM), and other forms of volatile memories known in the art. In some examples, memory 510 is used to store program instructions for execution by the processors 505. Memory 510, in one example, is used by software (e.g., the operating system 535 or applications 540). Generally, software applications 540 refer to software applications suitable for implementing at least some operations of the methods for providing EMRs as described herein.

One or more storage devices 515 can also include one or more transitory or non-transitory computer-readable storage media and/or computer-readable storage devices. In some embodiments, storage devices 515 may be configured to store greater amounts of information than memory 510. Storage devices 515 may further be configured for long-term storage of information. In some examples, the storage devices 515 include non-volatile storage elements. Examples of such non-volatile storage elements include magnetic hard discs, optical discs, solid-state discs, flash memories, forms of electrically programmable memories (EPROM) or electrically erasable and programmable memories, and other forms of non-volatile memories known in the art.

Still referencing to FIG. 5, the computer system 500 may also include one or more input devices 520. The input devices 520 may be configured to receive input from a user through tactile, audio, video, or biometric channels. Examples of input devices 520 may include a keyboard, keypad, mouse, trackball, touchscreen, touchpad, microphone, one or more video cameras, image sensors, fingerprint sensors, or any other device capable of detecting an input from a user or other source, and relaying the input to computer system 500, or components thereof.

The output devices 525, in some examples, may be configured to provide output to a user through visual or auditory channels. Output devices 525 may include a video graphics adapter card, a liquid crystal display (LCD) monitor, a light emitting diode (LED) monitor, an organic LED monitor, a sound card, a speaker, a lighting device, a LED, a projector, or any other device capable of generating output that may be intelligible to a user. Output devices 525 may also include a touchscreen, presence-sensitive display, or other input/output capable displays known in the art.

The computer system 500, in some example embodiments, also includes network interface 530. The network interface 530 can be utilized to communicate with external devices via one or more data networks such as one or more wired, wireless, or optical networks including, for example, the Internet, intranet, LAN, WAN, cellular phone networks, Bluetooth radio, and an IEEE 802.11-based radio frequency network, among others. The network interface 530 may be a network interface card, such as an Ethernet card, an optical transceiver, a radio frequency transceiver, or any other type of device that can send and receive information.

The operating system 535 may control one or more functionalities of computer system 500 and/or components thereof. For example, the operating system 535 may interact with the applications 540 and may facilitate one or more interactions between the applications 540 and components of the computer system 500. As shown in FIG. 5, the operating system 535 may interact with or be otherwise coupled to the application(s) 540 and components thereof. In some embodiments, application(s) 540 may be included in operating system 535. In these and other examples, virtual modules, firmware, or software may be part of the applications 540.

The terminology used herein is for the purpose of describing particular embodiments only and is not intended to be limiting of the technology. As used herein, the singular forms "a", "an" and "the" are intended to include the plural forms as well, unless the context clearly indicates otherwise. It will be further understood that the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that like or analogous elements and/or components, referred to herein, may be identified throughout the drawings with like reference characters. It will be further understood that several of the figures are merely schematic representations of the present disclosure. As such, some of the components may have been distorted from their actual scale for pictorial clarity.

In the foregoing description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. A system for providing electronic medical records (EMRs), the system comprising:
at least one processor and a memory storing processor-executable codes, wherein the at least one processor is configured to implement the following operations upon executing the processor-executable codes:
receiving a generic word-processing form template;
enabling completing data fields in the generic word-processing form template with data tags and action tags to generate an EMR form, the data tags and the action tags being used to enable retrieval and storage of clinical data associated with a patient, the clinical data being supplied via a user input or hospital records systems;
enabling signing the EMR form with one or more electronic signatures;
upon signing the EMR form, converting the EMR form into a digitized image, the digitized image including images of the one or more electronic signatures;
generating a hash based on the digitized image;
storing the signed EMR form in an EMR data repository; and
storing the hash to a blockchain system, wherein the hash is to be used to verify the signed EMR form by:
upon receiving a request to verify the signed EMR form, generating, based on the signed EMR form, a further digitized image;
generating a further hash based on the further digitized image; and
matching the further hash with the hash stored in the blockchain system.

2. The system of claim 1, wherein the clinical data are collected as the patient is being examined.

3. The system of claim 1, wherein the hospital records systems include hospital information systems, laboratory information systems, radiological information systems, and picture archiving and communication systems.

4. The system of claim 1, wherein the system further comprises an EMR data repository configured to store generic word-processing form templates, the clinical data, and EMR forms.

5. The system of claim 1, wherein the EMR form is shared on a limited time basis with other parties.

6. The system of claim 1, further comprising performing, using a machine learning model, one or more of descriptive analytics, predictive analytics, and prescriptive analytics on the clinical data.

7. The system of claim 6, wherein the descriptive analytics is performed using Power BI and the predictive analytics and the prescriptive analytics are performed using Azure Machine Learning or Microsoft Cognitive Toolkit.

8. The system of claim 6, wherein the descriptive analytics is performed using Tableau and the predictive analytics and the prescriptive analytics are performed using TensorFlow.

9. The system of claim 6, further comprising updating the machine learning model upon establishing connection to the Internet.

10. The system of claim 1, wherein the processor-executable codes are configured to run on one of: Windows based laptops, Android based tablets, or on iPads with Apple Pencil.

11. The system of claim 1, the processor-executable codes are configured to run as one of: a desktop application, a web application, a word application, or a mobile application.

12. The system of claim 1, wherein the user input is received via one of: a keyboard, a mouse, a handwriting device, and a voice input device.

13. The system of claim 1, wherein the clinical data are retrieved from hospital systems of records via at least one of application programming interface or a stored procedure.

14. The system of claim 1, further comprising a backup mechanism configured to backs up system data at predefined time intervals, the system data including one or more generic word-processing form templates, one or more EMR forms, and clinical data.

15. The system of claim 1, further comprising enabling sharing, via the blockchain system or a Fast Healthcare Interoperability Resources (FHIR) server, the system data to healthcare facilities.

16. The system of claim 1, wherein the data tags and the action tags are updated upon establishing connection to Internet.

17. The system of claim 1, wherein the EMR data repository includes a NoSQL database.

18. The system of claim 17, further comprising backing up the NoSQL database to one of: Microsoft Azure, Amazon Web Services, Google Cloud Platform upon establishing connection to Internet.

19. A computer-implemented method for providing electronic medical records (EMRs), the method comprising:
- receiving a generic word-processing form template;
- enabling completing data fields in the generic word-processing form template with data tags and action tags to generate an EMR form, the data tags and the action tags being used to enable retrieval and storage of clinical data associated with a patient, the clinical data being supplied via a user input or hospital records systems;
- enabling signing the EMR form with one or more electronic signatures;
- upon signing the EMR form, converting the EMR form into a digitized image, the digitized image including images of the one or more electronic signatures;
- generating, based on the digitized image, a hash;
- storing the signed EMR form in an EMR data repository; and
- storing the hash to a blockchain system, wherein the hash is to be used to verify the signed EMR form by:
  - upon receiving a request to verify the signed EMR form, generating, based on the signed EMR form, a further digitized image;
  - generating a further hash based on the further digitized image; and
  - matching the further hash with the hash stored in the blockchain system.

20. A non-transitory processor-readable medium having instructions stored thereon, which when executed by one or more processors, cause the one or more processors to implement a method for providing electronic medical records (EMRs), the method comprising:
- receiving a generic word-processing form template;
- enabling completing data fields in the generic word-processing form template with data tags and action tags to generate an EMR form, the data tags and the action tags being used to enable retrieval and storage of clinical data associated with a patient, the clinical data being supplied via a user input or hospital records systems;
- enabling signing the EMR form with one or more electronic signatures;
- upon signing the EMR form, converting the EMR form into a digitized image, the digitized image including images of the one or more electronic signatures;
- generating, based on the digitized image, a hash;
- storing the signed EMR form in an EMR data repository; and
- storing the hash to a blockchain system, wherein the hash is to be used to verify the signed EMR form by:
  - upon receiving a request to verify the signed EMR form, generating, based on the signed EMR form, a further digitized image;
  - generating a further hash based on the further digitized image; and
  - matching the further hash with the hash stored in the blockchain system.

\* \* \* \* \*